United States Patent [19]

Palmer

[11] Patent Number: 5,776,075
[45] Date of Patent: Jul. 7, 1998

[54] ENDOSCOPIC BIOPTOME JAW ASSEMBLY HAVING THREE OR MORE JAWS AND AN ENDOSCOPIC INSTRUMENT INCORPORATING SAME

[75] Inventor: Matthew A. Palmer, Miami, Fla.

[73] Assignee: Symbiosis Corporation, Miami, Fla.

[21] Appl. No.: 695,036

[22] Filed: Aug. 9, 1996

[51] Int. Cl.[6] ................................................ A61B 10/00
[52] U.S. Cl. ................................................ 600/564
[58] Field of Search ................................ 128/749, 751, 128/753; 606/205–208, 167; 600/104, 105, 562–568

[56] References Cited

U.S. PATENT DOCUMENTS

| | | | |
|---|---|---|---|
| 3,895,636 | 7/1975 | Schmidt. | |
| 4,467,802 | 8/1984 | Maslanka. | |
| 4,880,015 | 11/1989 | Nierman. | |
| 5,228,451 | 7/1993 | Bales et al. | |
| 5,269,780 | 12/1993 | Roos | 606/42 |
| 5,284,162 | 2/1994 | Wilk | 128/898 |
| 5,318,589 | 6/1994 | Lichtman | 128/751 X |
| 5,320,627 | 6/1994 | Sorenson et al. | 606/128 |
| 5,352,237 | 10/1994 | Rodak et al. | 128/751 X |
| 5,474,057 | 12/1995 | Makower et al. | 600/214 |
| 5,538,008 | 7/1996 | Crowe | 128/751 |
| 5,542,432 | 8/1996 | Slater et al. | |
| 5,562,102 | 10/1996 | Taylor | 128/751 |
| 5,638,827 | 6/1997 | Palmer et al. | |

*Primary Examiner*—Jennifer Bahr
*Assistant Examiner*—Samuel Gilbert
*Attorney, Agent, or Firm*—David P. Gordon; Thomas A. Gallagher; David S. Jacobson

[57] ABSTRACT

An endoscopic bioptome jaw assembly has at least thee jaws. In one embodiment the assembly includes at least three distally extending resilient arms. Each of the resilient arms terminates in a jaw which includes a substantially hollow distal jaw cup. The resilient arms are bent to urge each jaw away from the other. Each jaw cup has at its distal end at least one end tooth having a cutting edge. An endoscopic bioptome includes a tubular member having a displaceable wire extending therethrough. The proximal ends of the tubular member and wire are coupled to a manual actuation means for axially displacing the flexible member relative to the wire. The distal end of the tubular member is coupled to either a cylinder having a distal edge or to the base of the jaw assembly. The distal end of the wire is coupled to the other of the cylinder or the jaw assembly. Axial movement of one of the jaw assembly or cylinder relative to the other draws the arms into the cylinder or moves the cylinder over the arms to bring the jaw cups together in a biting action. When in a closed position the jaw cups form to a 360° hemispherical cup. In another embodiment, the jaw assembly includes at least three substantially rigid jaws coupled to a clevis having at least three radial slots and coupled to a push rod by hinged links.

22 Claims, 12 Drawing Sheets

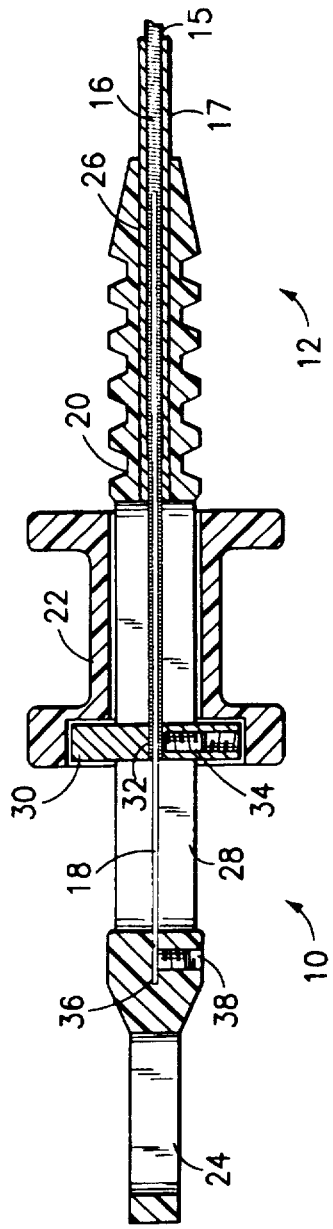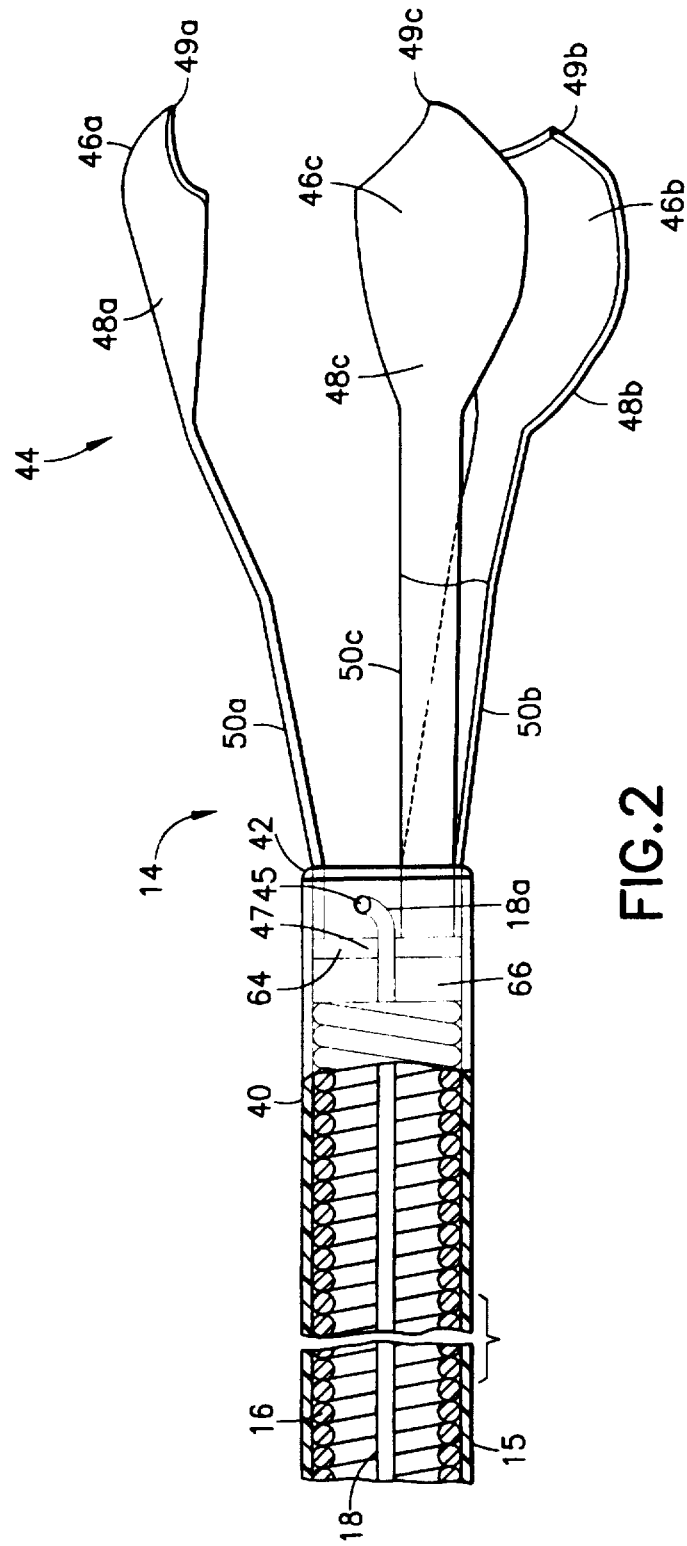

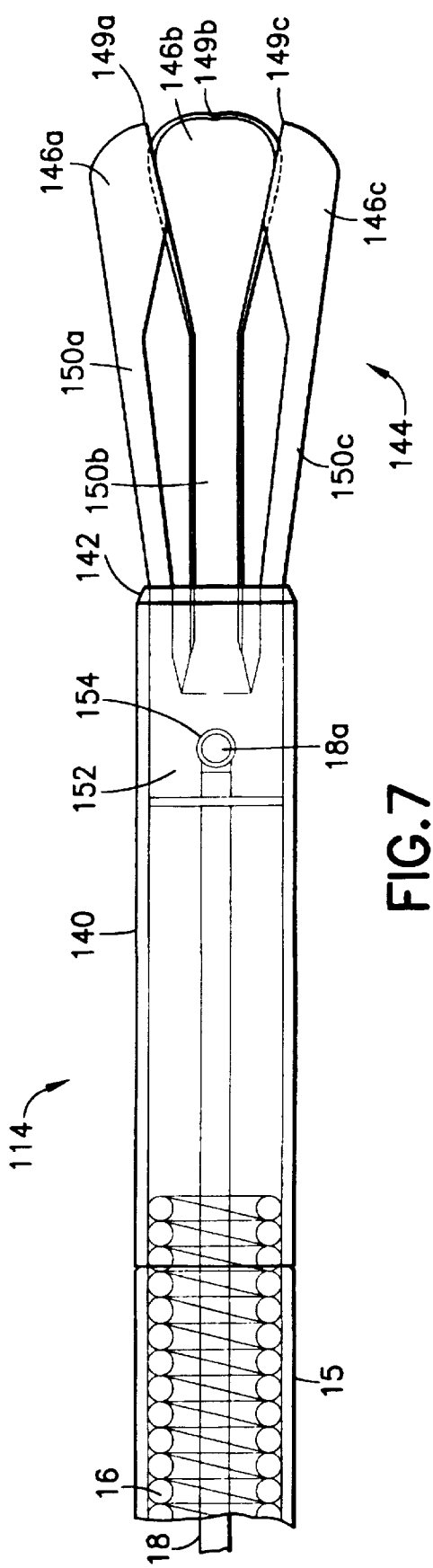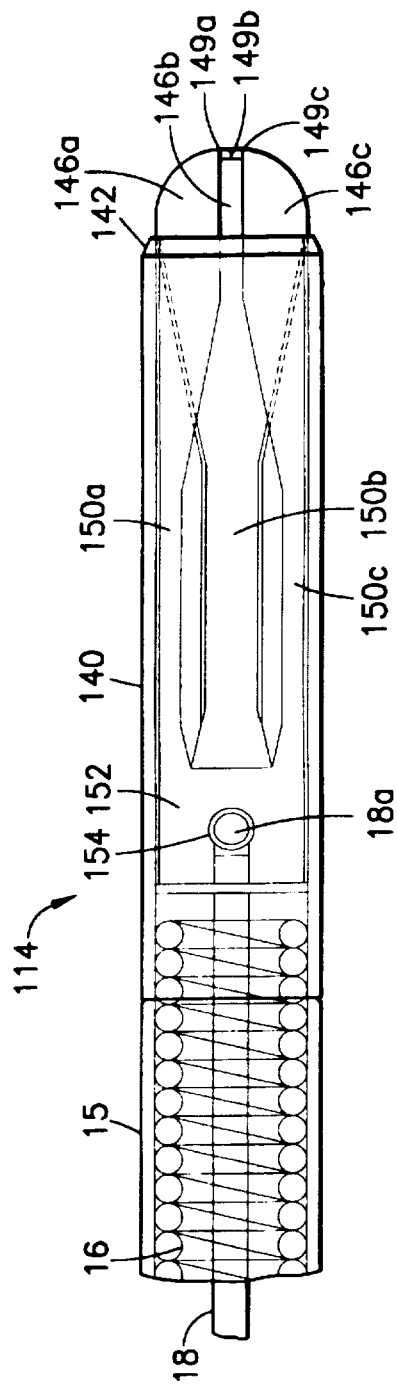
FIG.7
FIG.8

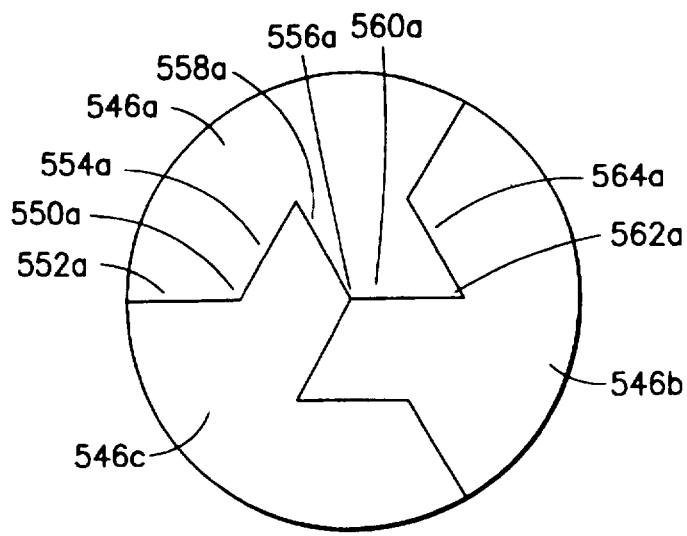
FIG.12
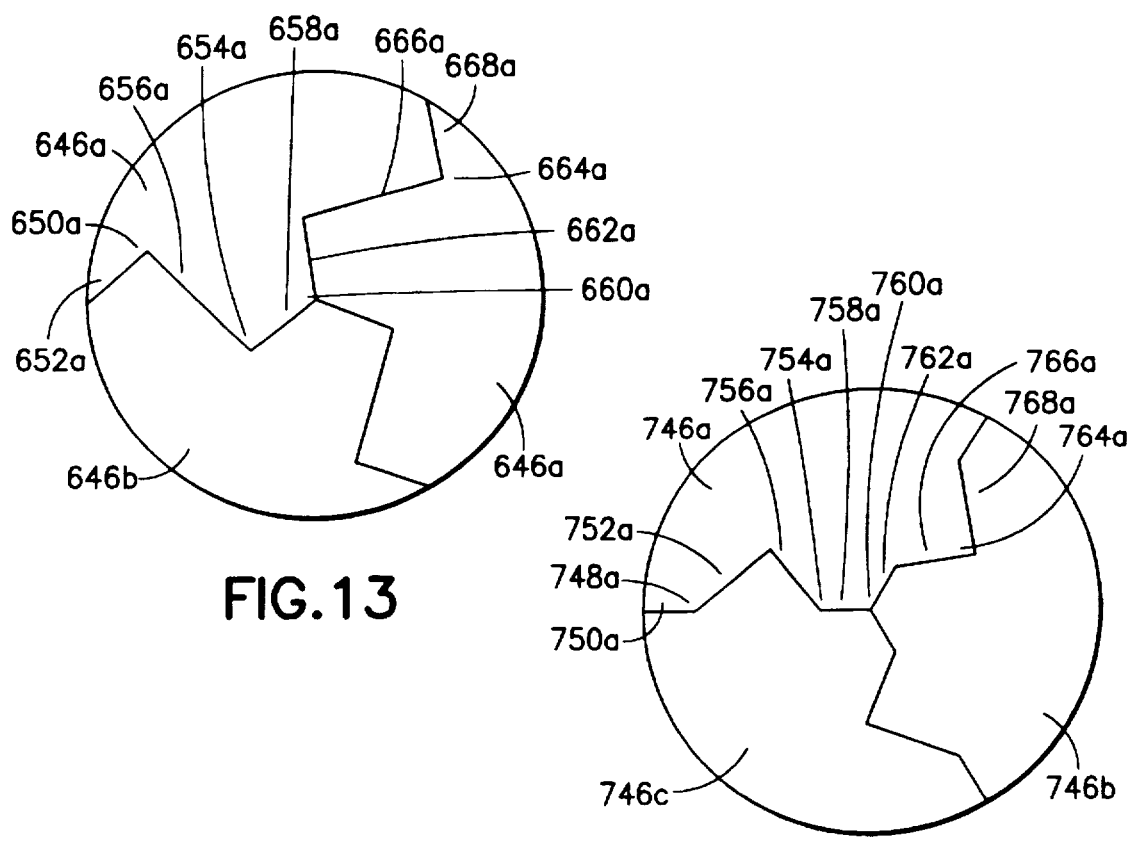
FIG.13
FIG.14

ENDOSCOPIC BIOPTOME JAW ASSEMBLY HAVING THREE OR MORE JAWS AND AN ENDOSCOPIC INSTRUMENT INCORPORATING SAME

This application is related to co-owned application Ser. No. 08/440,326, filed May 12, 1995, now U.S. Pat. No. 5,638,827 the complete disclosure of which is hereby incorporated by reference herein.

BACKGROUND OF THE INVENTION

1. Field of the Invention

The invention relates to endoscopic instruments. More particularly, the invention relates to biopsy forceps jaws. For purposes herein, the term "endoscopic" is to be understood in its broad sense to include laparoscopic, arthroscopic, and other microsurgical instruments whether or not used with an endoscope.

2. State of the Art

Endoscopic biopsy forceps are used for taking tissue samples from the human body for analysis. These forceps typically have a pair of generally hemispherical cupped jaws attached to both the distal end of a long flexible coil, and the distal end of an actuating means which opens and closes the jaws when the actuating means is manipulated by the practitioner. The endoscopic biopsy procedure is accomplished through an endoscope which is inserted into a body and guided by manipulation to the biopsy site. The endoscope typically includes a long narrow flexible tube carrying distal optical means and having a narrow lumen for receiving the biopsy forceps. The practitioner guides the endoscope to the biopsy site using the optical means and inserts the forceps, with jaws closed, through the lumen of the endoscope to the biopsy site. While viewing the biopsy site through the optical means of the endoscope, the practitioner opens the forceps jaws and carefully guides the jaws around a tissue to be sampled. When the jaws are in the correct position, the practitioner manipulates the actuating means and closes the jaws on the tissue to be sampled. The cupped jaws sever or grip a sample of the tissue in the space between the cupped jaws so that the sample may be removed (ripped away) from the biopsy site. The forceps are then withdrawn from the lumen of the endoscope while the jaws are kept shut, with the sample captured in the space between the cupped jaws.

The endoscopic biopsy procedure poses several challenges to the design and manufacture of the biopsy forceps instrument and particularly the biopsy forceps jaws. The jaws must be small enough to fit through the narrow lumen of the endoscope, yet strong enough and/or sharp enough to cut and/or tear tissue. An early example of an endoscopic biopsy forceps instrument is shown in U.S. Pat. No. 3,895,636 to Schmidt. The forceps in Schmidt include a pair of cupped toothless jaws with sharpened opposed edges intended to cut through tissue being sampled. Because of the miniature size of the jaws, however, it is difficult to sharpen the edges to a very high degree. Consequently, it is necessary to apply great force to the jaws in order to sever the tissue being sampled. In practice, sufficient force to sever the tissue is rarely achieved. Thus, either the jaws effect a clamping action which permits the tissue to be torn away from the biopsy site, or the jaws simply slip off the tissue without cutting or tearing it.

U.S. Pat. No. 4,880,015 to Nierman shows an endoscopic biopsy forceps instrument having opposed rectangularly cupped jaws with teeth on their parallel edges. When the jaws close, opposed teeth interleave providing a slightly better gripping ability than the jaws disclosed by Schmidt. However, the rectangular configuration of the jaws and the absence of teeth at the distal end of the jaws limits their functionality. Additionally, with these jaws and other toothed jaws, the teeth often do not align properly and prevent the jaws from closing completely which adds to the inefficiency of cutting and/or tearing and resultant slippage. Similarly, the misalignment of the opposed teeth sometimes causes the jaws to lock in the closed position.

Co-owned U.S. Pat. No. 5,228,451 to Bales et al., the complete disclosure of which is hereby incorporated by reference herein, discloses an endoscopic biopsy forceps instrument having a pair of opposed jaws with teeth which extend along an arced (radial) outer edge of each jaw. The teeth are offset by one-half pitch relative to the longitudinal center line of the jaw so that the upper jaw and lower jaw can be made from the same mold and still permit the teeth to align (interleave) when the jaws are closed. This arrangement of jaw teeth greatly improves the cutting and/or gripping (tearing) action of the forceps. However, even with these biopsy forceps slippage can occur and it is desirable to reduce the incidence of slippage, as slippage will either reduce the size of the tissue sample retrieved or prevent tissue from being retrieved altogether. Jaw slippage may also increase the length of the endoscopy procedure if the practitioner is required to reinsert the bioptome when enough tissue is not retrieved.

Those skilled in the art will also appreciate that the biopsy procedure requires an acute awareness of the alignment between the jaws of the bioptome and the tissue being sampled. The prior art forceps jaws create a "<" shape opening between the jaws when the jaws are in the open position. As a result, if possible, the surgeon must optimize the approach of the bioptome towards the tissue to be sampled so that the jaws are best aligned to the tissue for desired contact. For example, in a polypectomy procedure, the excision of a polyp is made more difficult when the cutting jaws can approach the polyp from a limited number of directions.

Furthermore, prior art bioptomes have a limited surface area for grabbing, cutting and/or tearing. In the prior art, the usable cutting surface is defined by the length of the cutting edge on the pair of jaws. Prior art designs have maximized the usable cutting surface within the limit of their respective forceps design. However, it is believed that one cause of slippage in the bioptomes of art is that jaws of the prior bioptomes exert the grabbing, cutting, and/or tearing force upon the tissue along substantially only one contact plane defined by the edge of the jaws.

SUMMARY OF THE INVENTION

It is therefore an object of the invention to provide a jaw assembly for an endoscopic bioptome where the jaws have a plurality of cutting edges.

It is also an object of the invention to provide a jaw assembly which has an excellent ability to grab, cut and/or tear tissue samples.

It is also an object of the invention to provide a jaw assembly which exerts its grabbing, cutting, and/or tearing forces in more than one plane upon the tissue to be sampled.

Another object of the invention is to provide an endoscopic bioptome which has a set of jaws having an increased surface area with which to grab, tear, and/or cut tissue samples.

A further object of the invention is to provide an endoscopic bioptome which reduces alignment considerations between the jaws and the tissue being sampled.

In accord with these objects which will be discussed in detail below, the endoscopic bioptome of the present invention broadly includes a tubular member and a control member extending through the tubular member, a jaw assembly having at least three jaw cups coupled to the distal end of one of the control member and the tubular member, an actuation handle, having a stationary member, coupled to the proximal end of either the control member or the tubular member, and a movable member, coupled to the proximal end of the other of the control member and the tubular member, such that moving the movable member relative to the stationary member imparts movement of the control member relative to the tubular member and thereby opens and closes the three jaws cups of the jaw assembly. When the jaw assembly is in a closed position, the jaw cups together form a hemispherical cup. When the jaws are in the open position, an ample opening is created to permit the jaws to surround a tissue sample. Upon moving the jaws from the open position into the closed position the jaws will move inward toward the tissue sample from at least three directions and offer at least three cutting planes, each plane defined by the meeting of opposed cutting edges of the jaw assembly. It will also be appreciated that a jaw assembly using three jaws will have a cutting surface area greater than that of an assembly using two jaws. According to presently preferred aspects of the invention, each jaw is identical and is provided with one or more end teeth having cutting edges. The jaws according to the invention have an increased surface area and have the ability to grab, cut and/or tear tissue samples in more than one plane. In addition, with the provided identical jaws, the jaws self-align with the tissue to be sampled.

According to several disclosed embodiments, the jaws are made of superelastic material and are opened and closed by sliding interaction with a cylindrical sleeve. According to another disclosed embodiment, the jaws are rigid members which are mounted on axles in a modified clevis having three or more mounting slots.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of the proximal end of a biopsy forceps instrument according to the invention;

FIG. 2 is an enlarged broken, partially transparent, side elevation view, in partial section, of a first embodiment of a jaw assembly according to the invention;

FIG. 7 is a view similar to FIG. 2 of a second embodiment of a jaw assembly with the jaws open;

FIG. 8 is a view similar to FIG. 7, but with the jaws closed;

FIG. 12 is an enlarged distal end view of a sixth embodiment of a jaw assembly in a closed position in which each jaw cup has a plurality of end teeth forming the cutting edge;

FIG. 13 is an enlarged distal end view of a seventh embodiment of a jaw assembly in the closed position in which each jaw cup has a plurality of end teeth forming the cutting edge;

FIG. 14 is an enlarged distal end view of an eighth embodiment of a jaw assembly in the closed position in which each jaw cup has a plurality of end teeth forming the cutting edge;

DETAILED DESCRIPTION OF THE PREFERRED EMBODIMENTS

Figure 3:
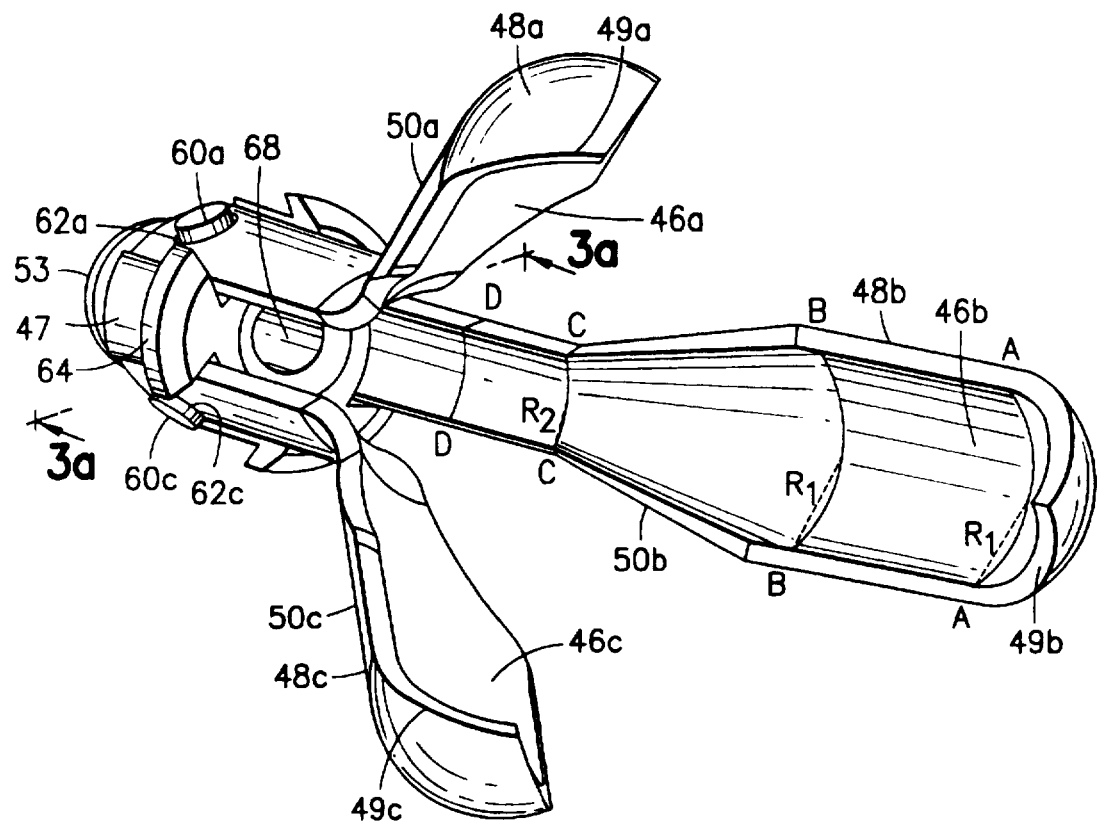
FIG. 3 is an enlarged isometric view of portions of the jaw assembly of FIG. 2 with the jaws open.
Figure 3A:
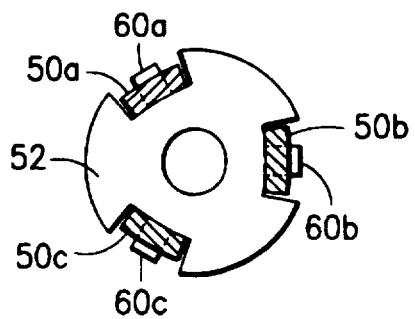
FIG. 3a is a sectional view taken along line 3a—3a in FIG. 3.

A first embodiment of a bioptome 10 of the invention is seen in FIGS. 1 and 2 and includes a proximal handle 12 and a distal end effector 14. A long flexible coil 16 having an axially displaceable control wire 18 extending therethrough couples the handle 12 and the end effector 14. The coil 16 is preferably covered with a PTFE, FEP or polyolefin sheath 15 along substantially all of its length and with a strain relief sleeve 17 covering a portion of the coil which extends from the handle 12. The control wire 18 is preferably flexible but longitudinally substantially inelastic and is ideally formed from 304 Steel and provided with and outer diameter of approximately 0.018 inch. The proximal handle 12 includes a central shaft 20 and a spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The spool 22 is provided with a cross member 30 which passes through the slot 28 in the central shaft 20. The cross member 30 is provided with a central through hole 32 and a radially engaging set screw 34. A short bore 36 and a radially engaging set screw 38 are provided in the shaft 20 distal of the thumb ring 24 with the bore 36 communicating with the longitudinal slot 28. The proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effector 14 as described in detail below.

Figure 4:
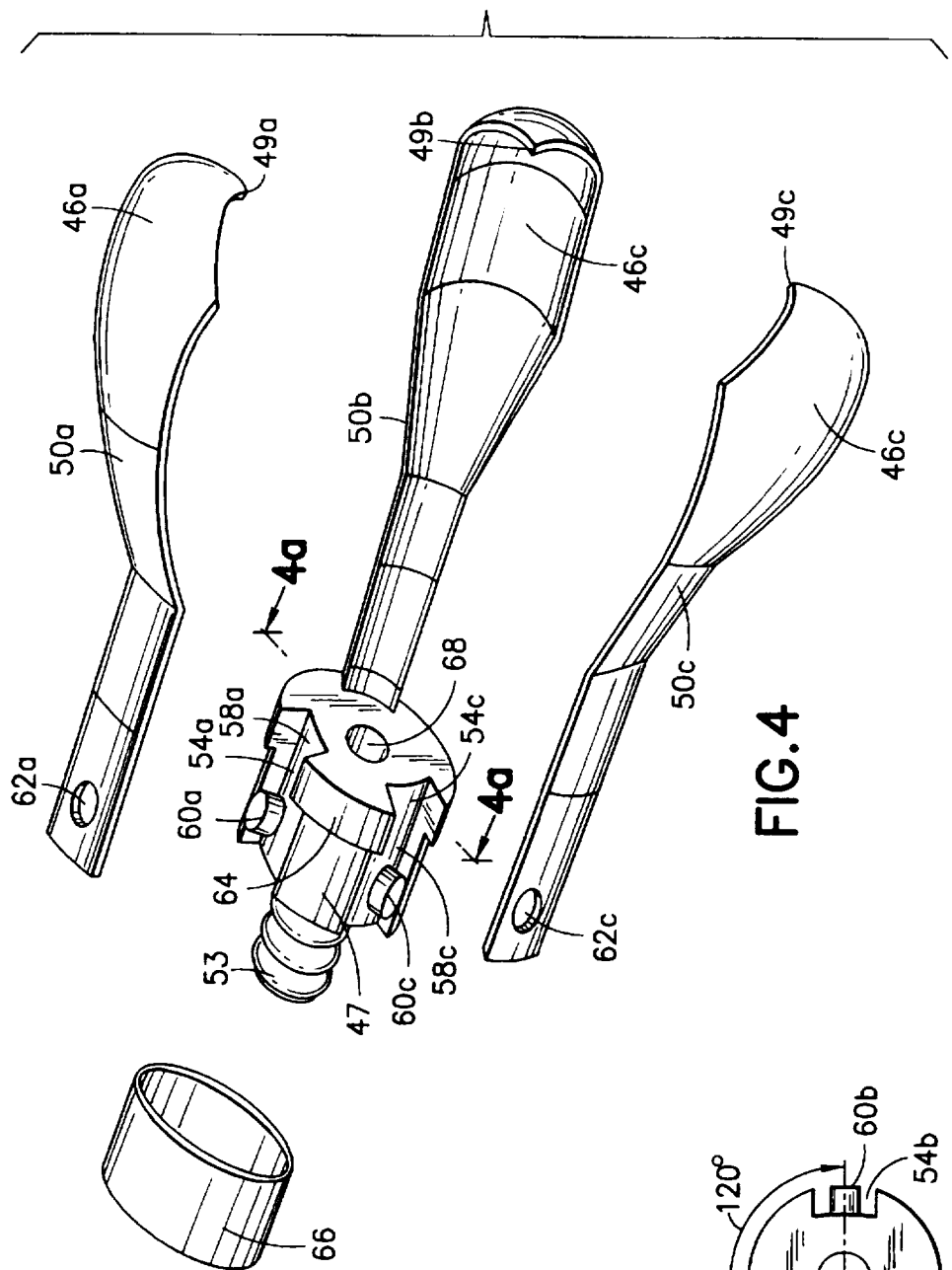
FIG. 4 is an enlarged exploded isometric view of the jaw assembly of FIGS. 2 and 3.
Figure 4A:
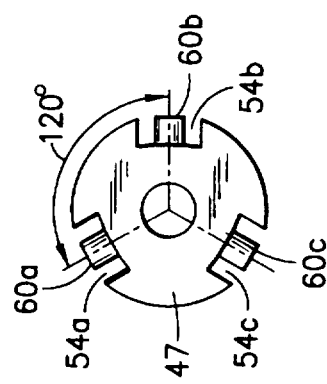
FIG. 4a is a sectional view taken along line 4a—4a in FIG. 4.
Figure 5:
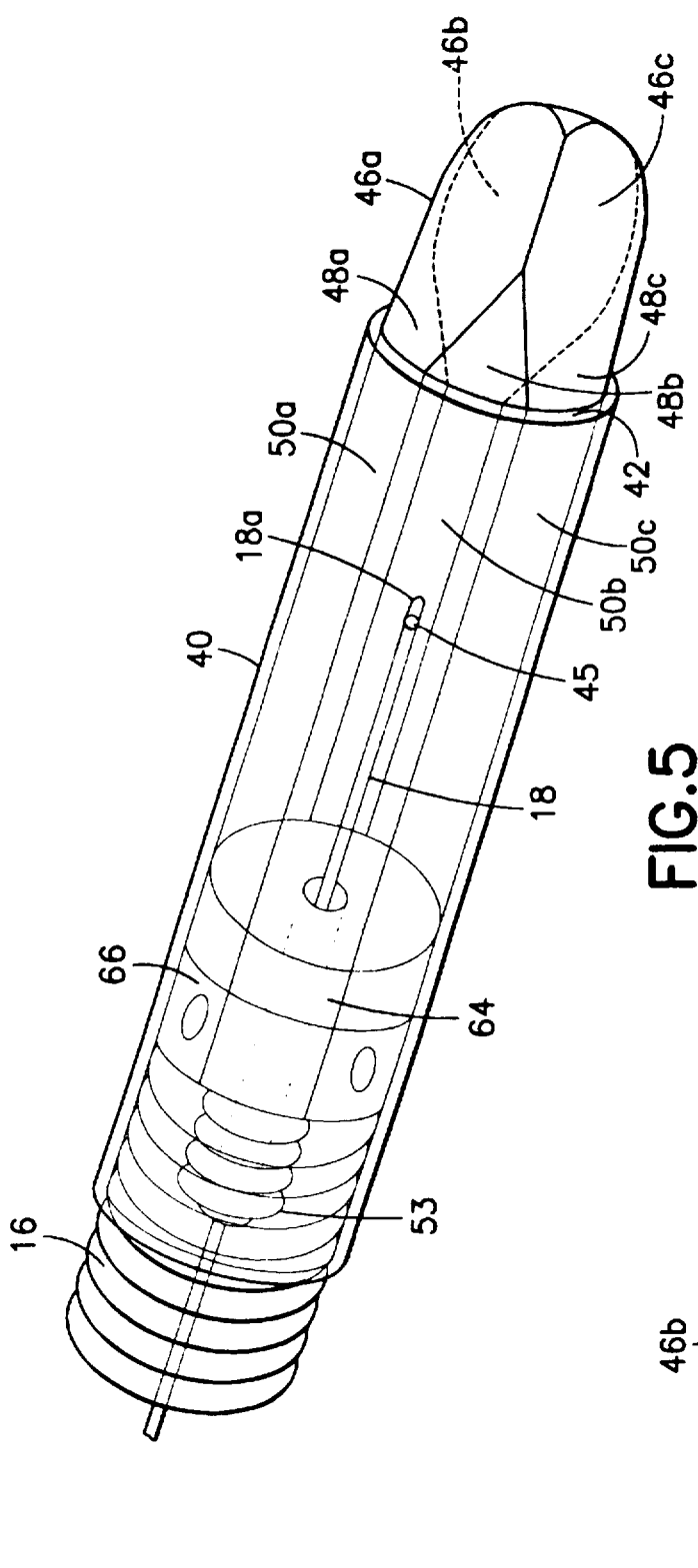
FIG. 5 is a broken enlarged partially transparent isometric view of the distal end of a biopsy forceps instrument of the invention with the jaws in the closed position.
Figure 5A:
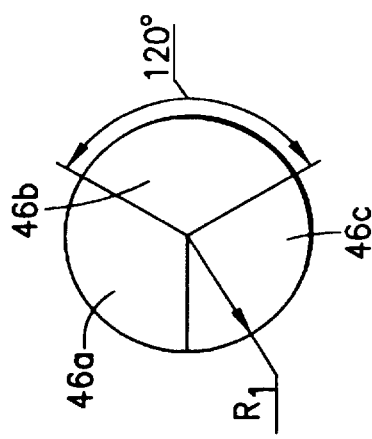
FIG. 5a is an enlarged distal end view of the jaws of FIG. 5 in the closed position.

Turning now to FIGS. 2 through 5a, the end effector 14 includes a cylindrical sleeve 40, having a distal end 42, and a jaw assembly 44. The jaw assembly includes a base member 47, a washer 66, and three jaws 48a, 48b, 48c each having a resilient, preferably narrow, arm 50a, 50b, 50c and terminating at its distal end in an identical jaw cup 46a, 46b, 46c. The jaw cups 46a, 46b, 46c terminate distally in a single sharp 120°-angled end tooth 49a, 49b, 49c so that when the jaw cups 46a, 46b, 46c are closed, the jaw cups form a hemispherical cup (FIG. 5). As shown in FIG. 3, distal of arc A—A, each jaw cup 46a, 46b, 46c has a shape defined by one-third of a hemisphere having a radius of R1. Between arcs A—A and B—B, each jaw cup has a shape defined by a 120° cylindrical segment also having a radius of R1. Between arcs B—B and C—C each jaw cup 46a, 46b, 46c tapers down from a radius of R1 into a resilient arm 50a, 50b, 50c of radius R2. The arms 50a, 50b, 50c and the jaws 48a, 48b, 48c are preferably of either Nitinol or spring steel, as disclosed in co-owned U.S. Pat. Ser. No. 08/440,326, which is hereby incorporated by reference herein, and are preferably bent apart from each other to urge the jaw cups 46a, 46b, 46c apart. This is shown best in FIG. 3 with the bend occurring between arcs C—C and D—D.

In a presently preferred embodiment of the invention, as shown in FIG. 4, the cylindrical base member 47 has three lengthwise channels or grooves 54a, 54b, 54c, with the longitudinal center of each channel located at 120° intervals around the circumference of the base member 47. The channel floor 58c, 58b, 58c or bottom of each channel 54a,54b, 54c has a protrusion 60a, 60b, 60c protruding slightly more than the thickness of each arm 50a, 50b, 50c. At the proximal end of each arm 50a, 50b, 50c, a mounting hole 62a, 62b, 62c is provided for cooperating with the protrusion 60a, 60b, 60c. As shown in FIG. 3, the arms 50a, 50b, 50c are coupled to the base member 47 by respectively fitting the arms into the channels 54a, 54b, 54c and respectively engaging the protrusions 60a, 60b, 60c with the mounting holes 62a, 62b, 62c. In addition, the distal end of the base member 47 includes a base member lip 64. The retaining washer 66 abuts against the base member lip 64 and secures the arms 50a, 50b, 50c to the base member 47 (FIGS. 4 and 5). The proximal end of the base member 47 is preferably provided with threads 53 so that the base member can be threaded into the distal end of the flexible coil 16. The base member 47 also contains a throughbore 54 through which the control wire 18 can extend.

As seen in FIGS. 2 and 5, the cylindrical sleeve 40 is coupled to the distal end of the control wire 18 by providing the sleeve 40 with a lateral hole 45 which receives a bent end 18a of the control wire 18. The bent end 18a of the control wire 18 is welded to the hole 45 in the side of the sleeve 40. The cylindrical sleeve 40 is slidably mounted over the cylindrical base member 47 of the jaw assembly and is axially movable over the resilient arms 50a, 50b, 50c.

From the foregoing description and with reference to FIGS. 1 through 5, those skilled in the art will appreciate that when the spool 22 and the shaft 20 are axially displaced relative to each other, the cylindrical sleeve 40 and the jaw assembly 44 are similarly axially displaced relative to each other, from the position shown in FIG. 2 to the position shown in FIG. 5 and vice versa. It will also be appreciated that when the spool 22 and shaft 20 are in the approximate position shown in FIG. 1, the cylindrical sleeve 40 and the jaw assembly 44 will be in the approximate position shown in FIG. 2; i.e., with the jaws open. Thus, those skilled in the art will further appreciate that when the thumb ring 24 is moved towards the spool 22, or vice versa, the cylindrical sleeve 40 and the jaw assembly 44 will be brought into the approximate position shown in FIG. 5; i.e., with the jaws closed.

It will be appreciated that when the jaw cups 46a, 46b, 46c are in the open position an ample opening is created to permit the jaw cups 46a, 46b, 46c to surround a tissue sample. Upon moving the jaws from the open position into the closed position the jaws will move inward toward the tissue sample from three directions and offer at least three cutting planes, the planes described by the cutting edges of the end teeth 49a, 49b, 49c of the jaw cups. It will also be appreciated that the jaw assembly 44 having three jaws will have a cutting surface area approximately fifty percent greater than that of an assembly using two jaws. As a result of the increased cutting surface area and the exertion of grabbing, cutting and/or tearing forces in greater than substantially one plane, the jaw assembly will have a greater ability to grab, cut and/or tear tissue samples. Furthermore, as each jaw cup is identical and distally terminates in one 120°-angled end tooth, the set of jaws will self-align without concern regarding the misalignment of cutting teeth.

Figure 6:
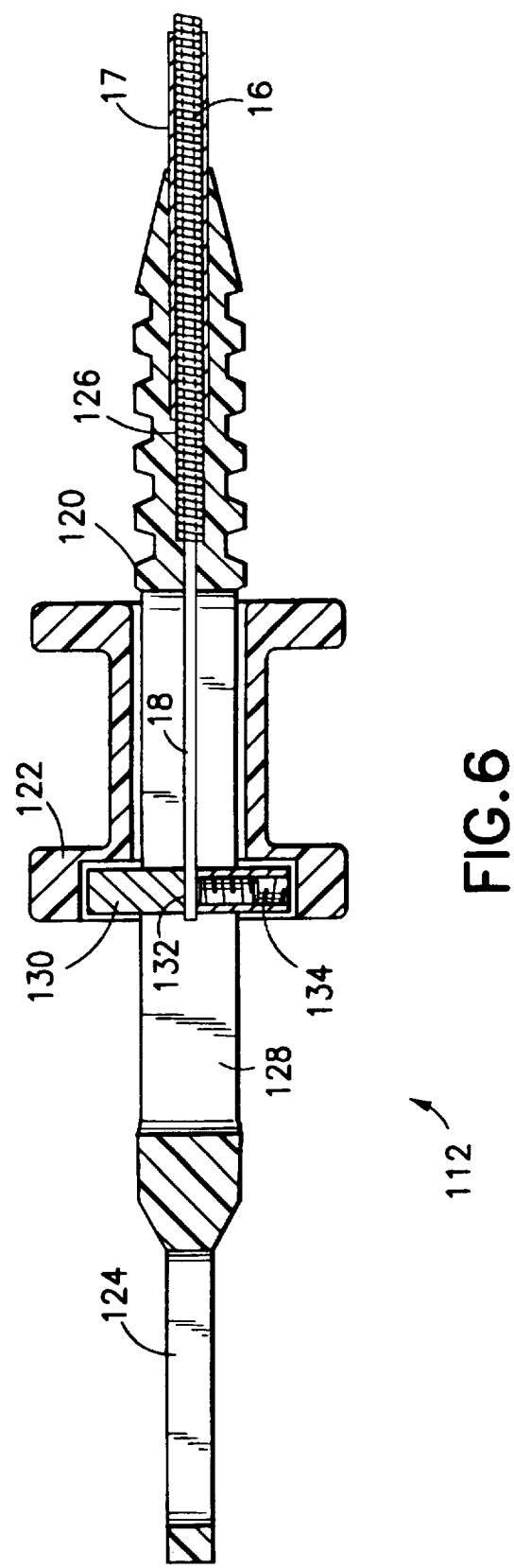
FIG. 6 is a view similar to FIG. 1 of the proximal end of a second embodiment of the invention.

A second embodiment of the bioptome is shown in FIGS. 6 through 8. In this embodiment, a proximal handle 112 and a distal end effector 114 are coupled by a long flexible coil 16 having an axially displaceable control wire 18 extending therethrough. The proximal handle 112 includes a central shaft 120 and a spool 122. The proximal end of the shaft 120 is provided with a thumb ring 124 and a stepped longitudinal bore 126 is provided at the distal end of the shaft 120. A longitudinal slot 128 extends from the proximal end of bore 126 to a point distal of the thumb ring 124. The spool 122 is provided with a cross member 130 which passes through the slot 128 in the central shaft 120. The cross member 130 is provided with a central hole 132 and a radially engaging set screw 134. According to this second embodiment of the invention, the proximal end of the coil 16 is fixedly mounted in the longitudinal bore 126 and the proximal end of the control wore 18 extends into the central hole 132 in the cross member 130 and is fixed there by the set screw 134. From the foregoing, those skilled in the art will appreciate that movement of the spool 122 relative to the shaft 120 results in movement of the control wire 18 relative to the coil 16. Such action results in actuation of the end effector 114 as described in detail below.

As seen in FIGS. 7 and 8, the end effector 114 according to the second embodiment of the invention includes a cylindrical sleeve 140 having a distal end 142 and a jaw assembly 144. The jaw assembly 144 includes a pair of opposed jaw cups 146a, 146b, 146c each having an end tooth 149a, 149b, 149c. A resilient, preferably narrow arm 150a, 150b, 150c extends proximally from each jaw cup 146a, 146b, 146c. A cylindrical base member 152 joins the proximal ends of the arms 150a, 150b, 150c. As seen best in FIG. 7, the narrow resilient arms 150a, 150b are bent apart from each other urging the jaw cups 146a, 146b, 146c apart. According to the second embodiment of the invention, the proximal end of the cylindrical sleeve 140 is coupled to the distal end of the flexible coil 16 by welding, soldering, crimping, or any other suitable manner. The cylindrical base member 152 of the jaw assembly 144 is coupled to the distal end of the control wire 18 by providing the base member 152 with a lateral hole 154 which engages a bent end 18a of the control wire 18 in a manner similar to that shown in FIG. 2 in the description of the first embodiment of the invention. However, as will be described in detail herein below, other methods of coupling the control wire to the base member are possible. The base member 152 and thus the entire jaw assembly 144 is slidably mounted and axially movable within the cylindrical sleeve 140 as shown in FIGS. 7 and 8. Those skilled in the art will appreciate that this second embodiment of the invention is quite similar to the first embodiment described above except that the sleeve 140 is coupled to the coil 16 which is coupled to the central shaft 120 of the handle 112, and the jaw assembly 144 is coupled to the control wire 18 which is coupled to the spool 122. Operation of this embodiment is substantially the same as the first embodiment described above.

The jaws 144 of the second embodiment multiple sample bioptome of the invention may be formed in different ways. According to one preferred embodiment, a cylinder of 304 or 17-7 stainless spring steel preferably having a diameter just slightly smaller than the diameter of the sleeve 140 is deep drawn to provide an enclosed hemispherical bottom. The bottom of the cylinder is then cut using wire electrical discharge machining (EDM) and/or laser machining. Preferably, reciprocal end teeth are cut into the periphery of the cylinder bottom, thereby forming the opposed jaw cups. The jaws are then bent away from each other to provide pre-loaded springy arms (i.e., leaf spring beams) which can be closed by the sleeve 140 as described above. Alternatively, Nitinol arms are formed to the desired shape.

Figure 9:
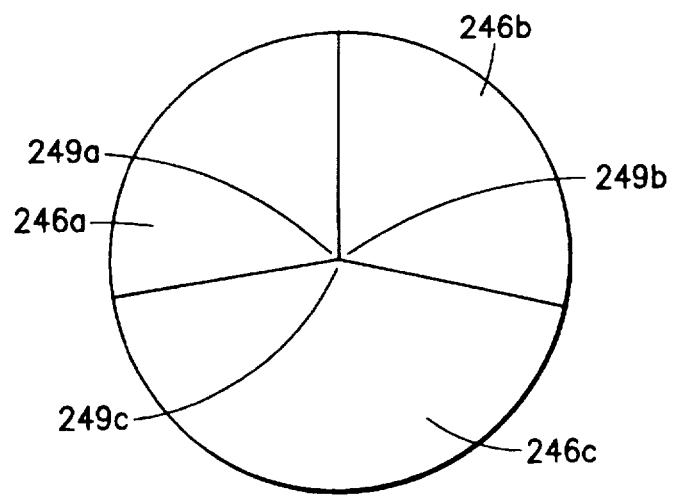
FIG. 9 is an enlarged distal end view of a third embodiment of a jaw assembly in the closed position in which one jaw cup is larger than two smaller jaw cups.
Figure 10:
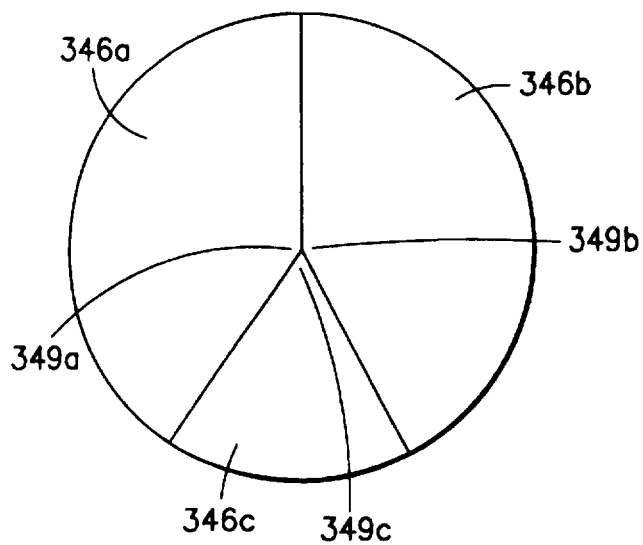
FIG. 10 is an enlarged distal end view of a fourth embodiment of a jaw assembly in the closed position in which one jaw cup is smaller than two larger jaw cups.
Figure 11:
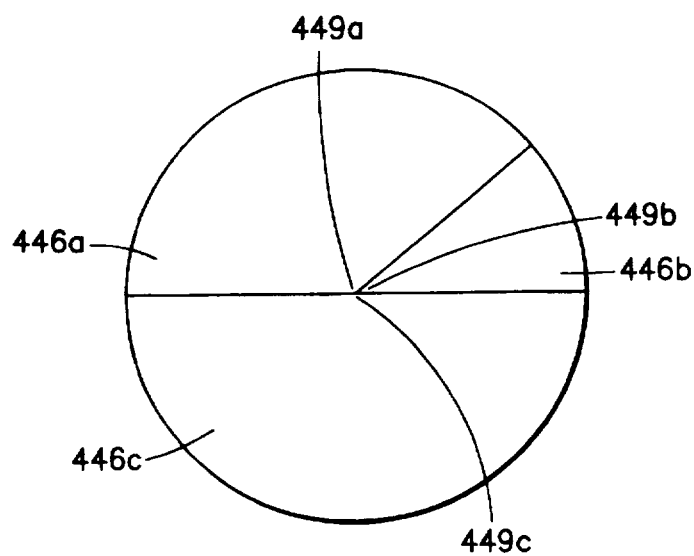
FIG. 11 is an enlarged distal end view of a fifth embodiment of a jaw assembly in the closed position in which each of three jaw cups is different in size.

Turning now to FIG. 9, a third embodiment of the jaw assembly of the invention is illustrated in which two identical smaller jaw cups 246a, 246b and one larger jaw cup 246c, are provided in the jaw assembly. The angle at the end teeth 249a, 249b on smaller jaw cups 246a, 246b is less than 120°, while the angle at the end tooth 249c of the larger jaw cup 248c is greater than 120°. FIG. 10 illustrates a fourth embodiment of the jaw assembly of the invention in which two identical larger jaw cups 346a, 346b and one smaller jaw cup 346c are provided in the jaw assembly. The angles at the end teeth 349a, 349b on larger jaw cups 346a, 346b are greater than 120° each. The angle of the end tooth 349c of the smaller jaw cup 348c is less than 120°. In FIG. 11 a fifth embodiment of the jaw assembly of the invention is shown in which three jaw cups 448a, 448b, 448c each have a non-identical angle at an end tooth 449a, 449b, 449c. With each of the above embodiments, it will be appreciated that when the jaw cups are in a closed position, the jaw cups form a hemispherical cup.

It is not necessary that the distal portion of the jaw cups be defined by only one end tooth. Rather, the distal portion of the cup may have several end teeth apexes formed by multiple cutting edges angled relative to each other. The cutting edges fit together to form a hemispherical cup. Referring to FIG. 12, a sixth embodiment of the jaw assembly of the invention is illustrated in which three identical cups 546a, 546b, 546c each have three tooth apexes. With reference to cup 546a, the first tooth apex 550a is defined by two cutting edges 552a, 554a angled 120° relative to each other. The second tooth apex 556a is defined by two cutting edges 558a, 560a angled 120° relative to each other. The third tooth apex 562a is defined by two cutting edges 560a, 564a angled 60° relative to each other.

FIG. 13 shows a seventh embodiment of the jaw assembly of the invention in which the jaw cups 646a, 646b, 646c each have four tooth apexes. With respect to the jaw cup 646a, the first tooth apex 650a is defined by a cutting edge 652a angled 120° relative to another edge (not shown). The second tooth apex 654a is defined by a two cutting edges 656a, 658a angled 90° relative to each other. The third tooth apex 660a is defined by two cutting edges 658a, 662a angled 120° relative to each other. The fourth tooth apex 664a is defined by two cutting edges 666a, 668a angled 90° relative to each other.

FIG. 14 shows an eighth embodiment in which the jaw cups 746a, 746b, 746c each have four tooth apexes. With respect to jaw cup 746a, the first tooth apex 748a is defined by two cutting edges 750a, 752a angled 120° relative to each other. The second tooth apex 754a is defined by two cutting edges 756a, 758a angled 120° relative to each other. The third tooth apex is defined by two cutting edges 758a, 762a angled 120° relative to each other. The fourth tooth apex 764a is defined by two cutting edges 766a, 768a angled 60° relative to each other.

Figure 15:
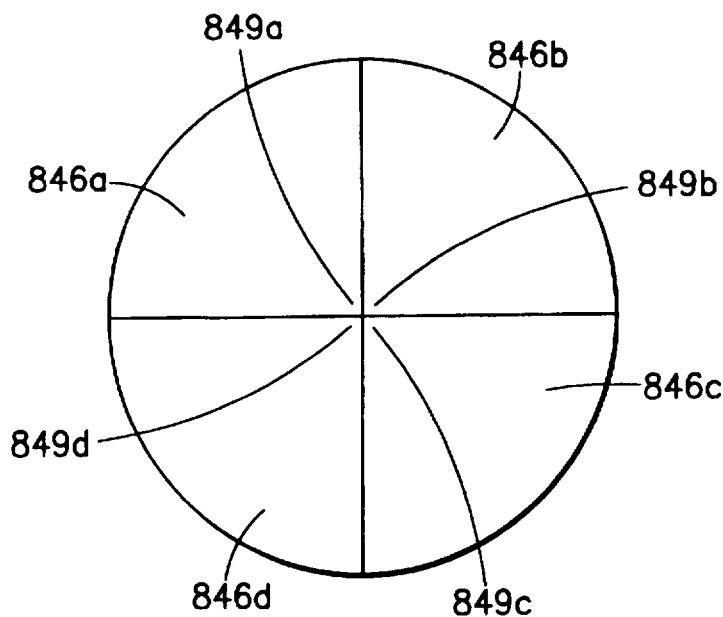
FIG. 15 is an enlarged distal end view of a ninth embodiment of a jaw assembly in the closed position having four identical jaw cups.
Figure 16:
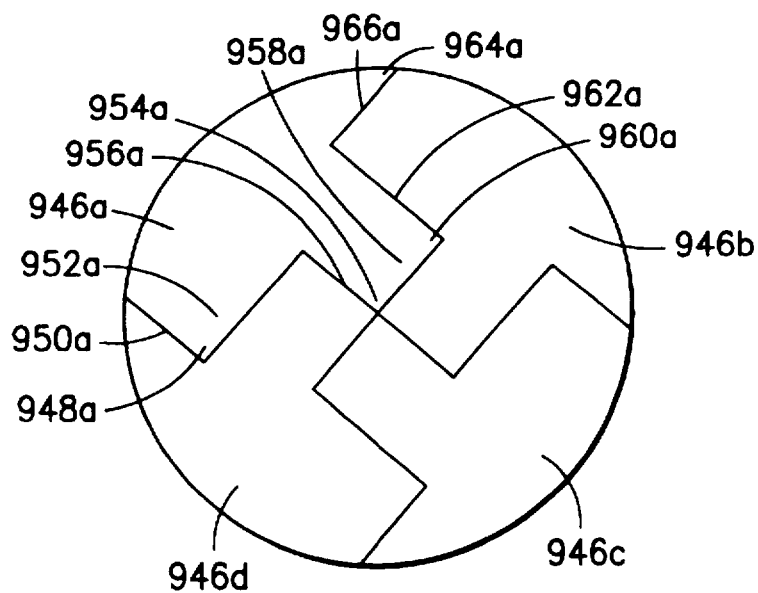
FIG. 16 is an enlarged distal end view of a tenth embodiment of a jaw assembly in the closed position in which each jaw cup has a plurality of end teeth forming the cutting edge.

Additionally, more than three jaws can be used in the jaw assembly. Turning to FIG. 15, a ninth embodiment of the jaw assembly of the invention is illustrated in which four identical jaws each have a jaw cup 846a, 846b, 846c, 846d having a single end tooth 849a, 849b, 849c, 849d with a 90° cutting edge. Furthermore, FIG. 16 shows a tenth embodiment of a jaw assembly in which each identical jaw cup 946a, 946b, 946c, 946d has multiple angular cuts forming several end teeth. With respect to jaw cup 946a, the first tooth apex is defined by two cutting edges 950a, 952a angled 90° relative to each other. The second tooth apex 954a is defined by two cutting edges 956a, 958a angled 90° relative to each other. The third tooth apex 960a is defined by two cutting edges 958a, 962a angled 90° relative to each other. The fourth tooth apex 964a is defined by a cutting edge 966a angled 120° relative to an edge (not shown). In each of the above embodiments it will likewise be appreciated that when the jaw cups are in the closed position, the jaw cups form a hemispherical cup. Furthermore, it is preferred that the cutting edges are sharp and provide a suitable cutting surface. However, it will be appreciated that the cutting edges may also be serrated which will also enable the jaws to elicit a cutting action.

Thus far, the jaw assemblies according to the invention have included jaws with elastic arms which are opened and closed by interaction with a cylindrical sleeve. According to an eleventh embodiment of the invention, a rigid jaw assembly and a modified clevis are provided.

Turning now to FIGS. 17–21, a jaw assembly 1000 according to the invention includes three rigid jaws 1002, 1004, 1006 and a modified clevis 1008. As described in more detail below, each jaw is hingedly coupled to the clevis 1008 and is coupled to the distal end of a push rod (or control wire) 1010 by a respective hinge link 1012, 1014, 1016.

Figure 17:
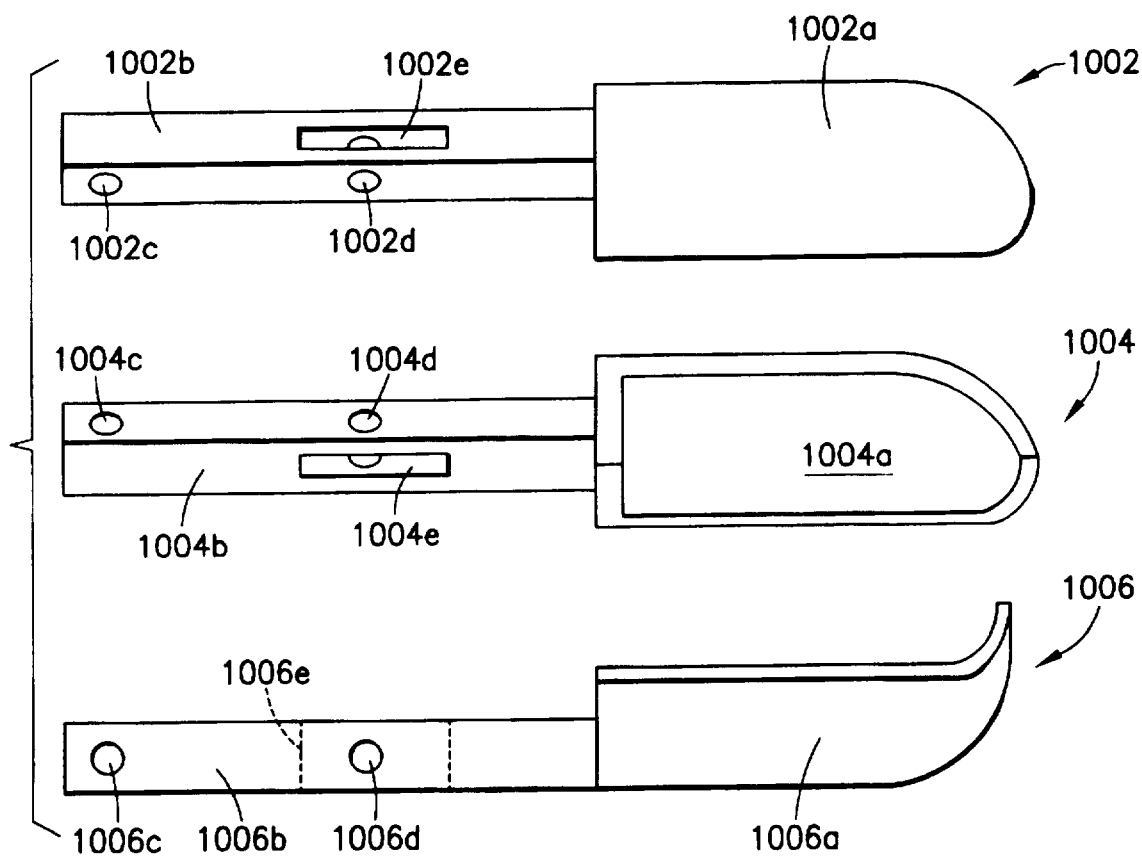
FIG. 17 is an enlarged exploded perspective view of the jaws of an eleventh embodiment of a jaw assembly.

As seen best in FIG. 17, each jaw has a distal jaw cup 1002a, 1004a, 1006a and a proximal tang 1002b, 1004b, 1006b. Each tang has a proximal mounting hole 1002c, 1004c, 1006c for hingedly coupling the jaw to the clevis 1008 and a central coupling hole 1002d, 1004d, 1006d. In addition, each tang is preferably provided with a central slot 1002e, 1004e, 1006e which intersects the respective coupling hole 1002d, 1004d, 1006d for receiving a respective hinge link 1012, 1014, 1016.

Figure 18:
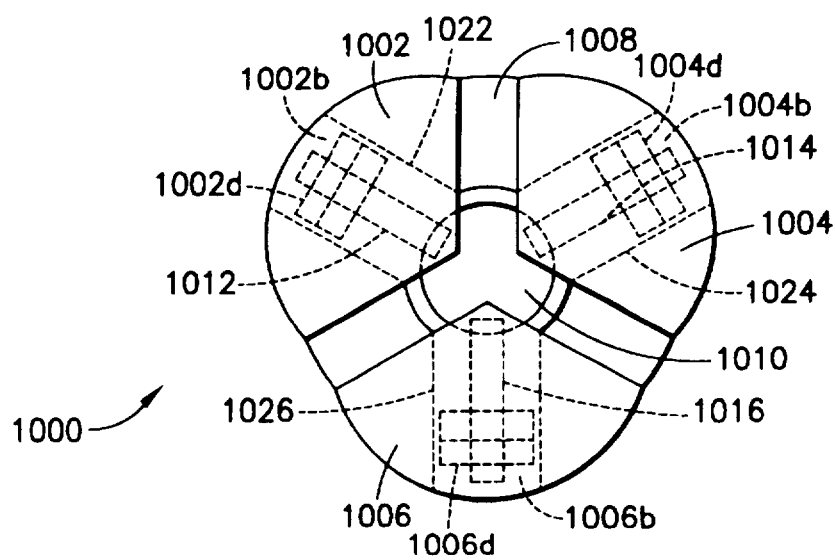
FIG. 18 is an enlarged distal end view of the eleventh embodiment of a jaw assembly showing the jaws in a partially opened position.
Figure 19:
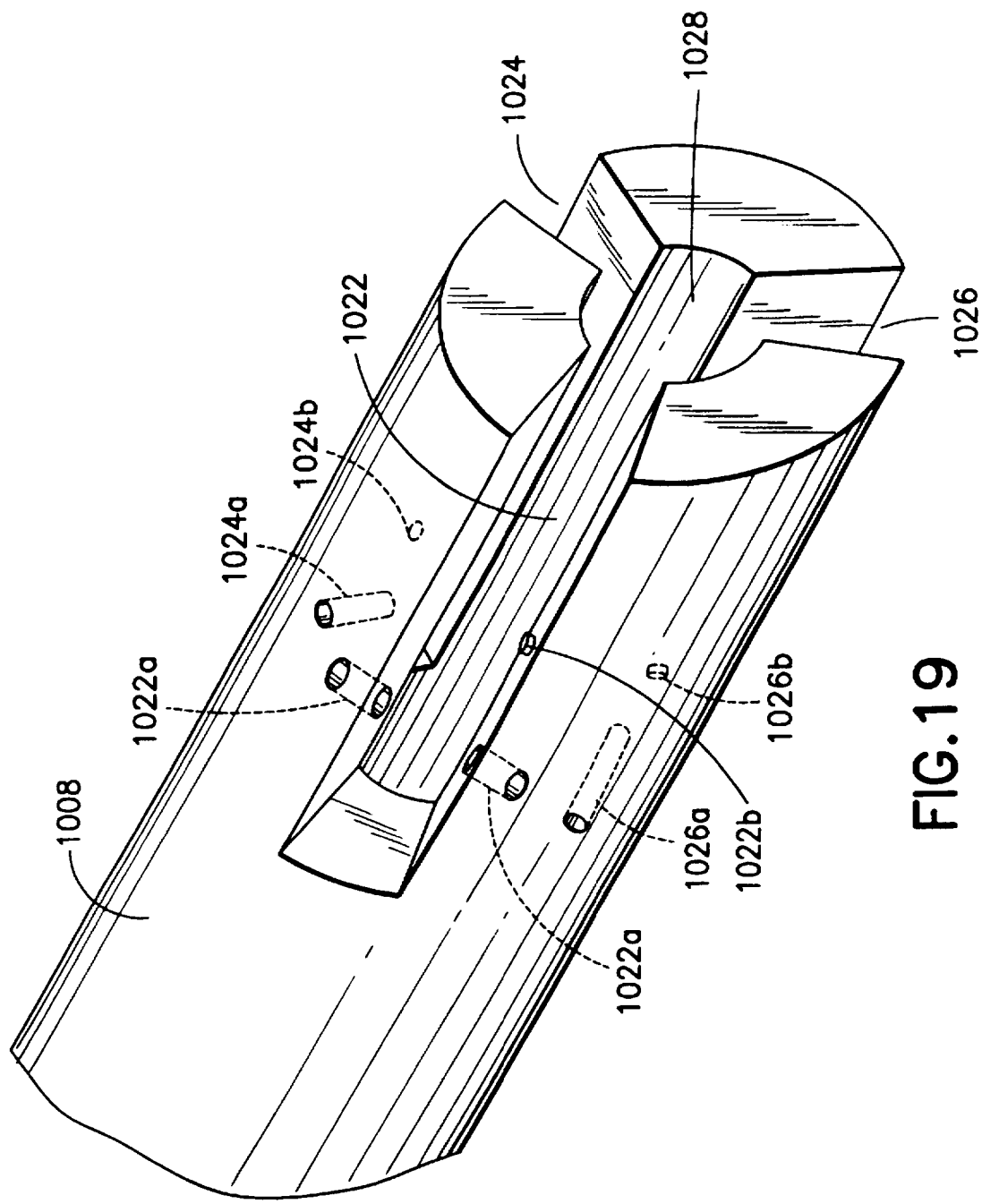
FIG. 19 is an enlarged broken isometric view of the clevis of the eleventh embodiment of a jaw assembly.
Figure 20:
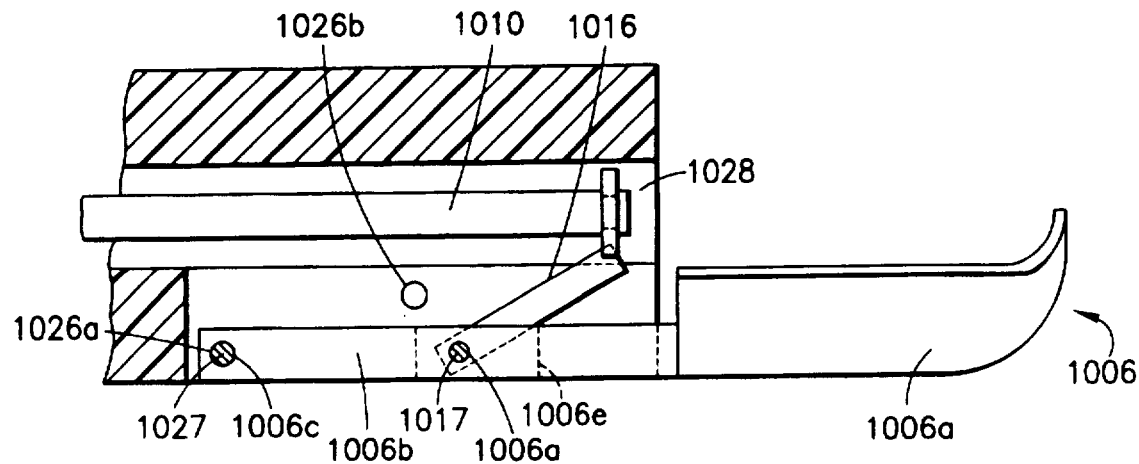
FIG. 20 is a broken enlarged sectional view showing one of the jaws in the closed position.
Figure 21:
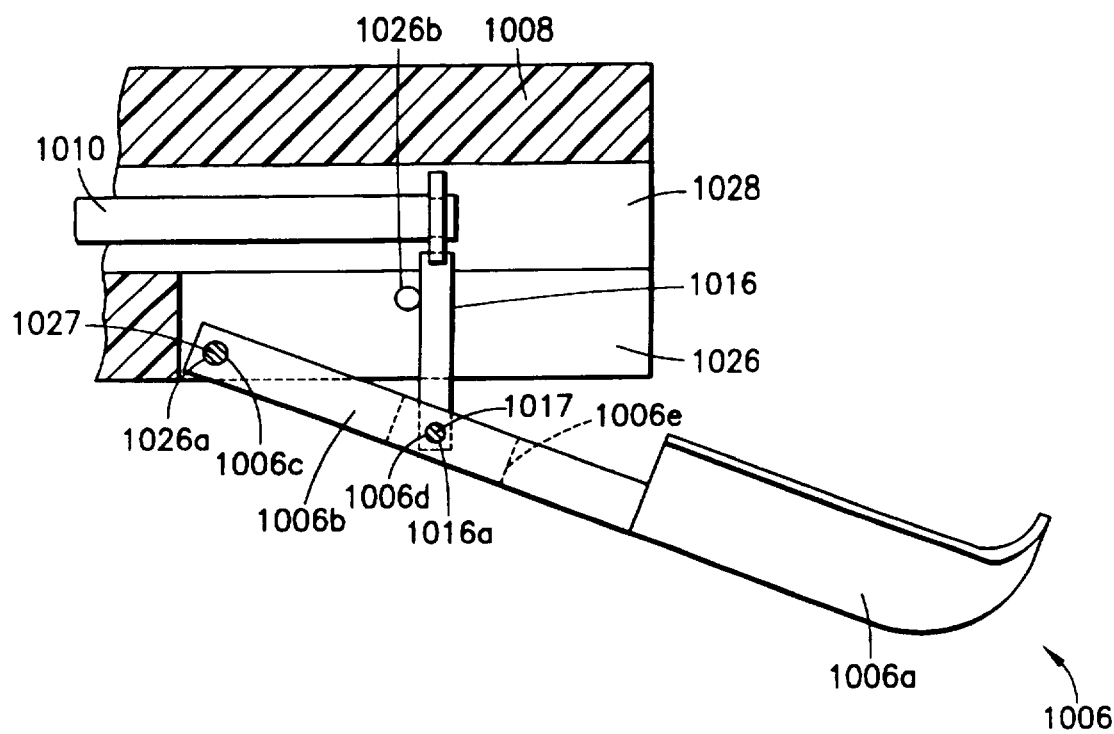
FIG. 21 is a view similar to FIG. 20 with the jaw in the open position.

As seen best in FIG. 19, the clevis 1008 is provided with three radial slots 1022, 1024, 1028 for receiving the respective tangs of jaws 1002, 1004, 1006 and a central bore 1028 for receiving the push rod or control wire 1010 (FIGS. 18, 20, and 21). Each slot 1022, 1024, 1028 is intersected by a proximal axle receiving bore 1022a, 1024a, 1026a and a link stop 1022b, 1024b, 1026b.

The coupling of the jaws to the clevis and the push rod is seen best in FIGS. 20 and 21, with respect to the jaw 1006. The tang 1006b of the jaw is inserted in the slot 1026 so that its mounting hole 1006c aligns with the axle bore 1026a and an axle 1027 is press fit in the bore 1026a to hingedly attach the jaw to the clevis. The push rod 1010 is provided with three hinged links 1012, 1014, 1016 as described above and seen best in FIG. 18. The hinged link 1016 extends through the slot 1026 and into the slot 1006e in the tang 1006b of the jaw 1006. The distal end of the hinged link 1016 is provided with a coupling hole 1016a which is aligned with the coupling hole 1006d in the tang 1006b and a pivot axle 1017 is press fit in the hole 1006d to hingedly couple the tang 1006b with the link 1016.

As seen in FIGS. 20 and 21, when the push rod 1010 is moved proximally, the hinged link 1016 is forced radially outward to urge the jaw 1016 against its pivot coupling 1006c to the open position shown in FIG. 21. In order to prevent the link 1016 from folding back inward, the stop 1026b is provided in the slot 1026 so that the link abuts the stop when the link is aligned substantially radially relative to the clevis 1008. It will also be appreciated that when the push rod 1010 is moved distally from the position shown in FIG. 21 to the position shown in FIG. 20, the jaw 1006 is hinged into the closed position. Although not shown in detail, each of the jaws 1002, 1004, and 1006 operates in substantially the same manner.

There have been described and illustrated herein several embodiments of a jaw assembly for an endoscopic bioptome. While particular embodiments of the invention have been described, it is not intended that the invention be limited thereto, as it is intended that the invention be as broad in scope as the art will allow and that the specification be read likewise. Thus, while particular coupling of the arms to a base member has been disclosed, it will be appreciated that other types of couplings could be utilized. Furthermore, while the distal end of the control wire has been shown to be coupled to the sleeve by welding, it will be understood that another manner of coupling can be used. It will also be understood that the control wire may, in the alternative, be coupled to the base member of the jaw assembly and that the sleeve may be fixed to the distal end of the coil. In addition, while threading has been disclosed as the preferred manner for coupling the base member to the coil, any suitable manner may be used including but not limited to welding, soldering, crimping. Furthermore, other actuator handles known in the art for endoscopic biopsy forceps instruments may also be used to move the jaws from an open position to a closed position. It will also be appreciated that all of the embodiments of the present bioptome can be provided with a cautery capability. Where superelastic materials are used to form the jaw cups, portions of the jaw cups can be coated with a more conductive metal to enhance the cautery function. With regard to the hinged rigid jaws, it will be understood that other coupling arrangements may be provided and that more than three jaws may be used. It will therefore be appreciated by those skilled in the art that yet other modifications could be made to the provided invention without deviating from its spirit and scope as so claimed.

We claim:

1. A jaw assembly for an endoscopic biopsy forceps instrument having a tubular member, a control wire extending through the tubular member, and an actuation means coupled to the control wire and the tubular member for moving one of the control wire and the tubular member relative to the other of the control wire and the tubular member, said jaw assembly comprising:

a) at least three jaws, each having a distal jaw cup; and b) a base member means discrete from the control wire, the jaws, and the tubular member for coupling said at least three jaws to one of the control wire and the tubular member, wherein relative movement of the control wire and the tubular member moves said distal jaws cups from a first open position to a second closed position.

2. A jaw assembly according to claim 1, further comprising:

washer means for coupling said base member means to said resilient arms, wherein said base member means has channel means for receiving said resilient arms, and said washer means seats over said base member means and secures said resilient arms in said channel means.

3. A jaw assembly according to claim 1, wherein:

said jaw cups substantially form a hemisphere when in said second closed position.

4. A jaw assembly according to claim 1, wherein:

said jaw assembly includes exactly three laws.

5. A jaw assembly according to claim 4, wherein:

each of said three law cups has one tooth having an apex angle of approximately 120°.

6. A jaw assembly according to claim 1, wherein:

said jaws are substantially identical.

7. A jaw assembly for an endoscopic biopsy forceps instrument having a tubular member, a control wire extending through the tubular member, and an actuation means coupled to the control wire and the tubular member for moving one of the control wire and the tubular member relative to the other of the control wire and the tubular member, said jaw assembly comprising:

a) at least three jaw, each having a distal jaw cup and each having a resilient arm;

b) a base member means discrete from the control wire, and the tubular member for coupling said at least three jaws to one of the control wire and the tubular member; and c) a cylinder having a distal edge and adapted to be coupled to a distal end of the other of one of the control wire and the tubular member, each said resilient arm extending into said cylinder, wherein relative movement of the control wire and the tubular member moves said distal laws cups from a first open position to a second closed position, and wherein relative movement of one of the control wire and the tubular member relative to each other moves one of said cylinder and said resilient arms relative to each other such that said distal edge of said cylinder contacts said resilient arms to move said distal jaw cups from said first open position to said second closed position.

8. A jaw assembly for an endoscopic biopsy forceps instrument having a tubular member, a control wire extending through the tubular member, and an actuation means coupled to the control wire and the tubular member for moving one of the control wire and the tubular member relative to the other of the control wire and the tubular member, said jaw assembly comprising:

a) at least three jaws, each having a distal jaw cup, and each of said jaw cups having a plurality of teeth; and b) a base member means discrete from the control wire and the tubular member for coupling said at least three jaws to one of the control wire and the tubular member, wherein relative movement of the control wire and the tubular member moves said distal jaws cups from a first open position to a second closed position.

9. A jaw assembly for an endoscopic biopsy forceps instrument having a tubular member, a control member extending through the tubular member, and actuation means coupled to the control member and the tubular member for moving the control member and the tubular relative to each other, said jaw assembly, comprising:

at least three substantially rigid jaws, each jaw having a distal jaw cup and a proximal tang;

a clevis having at least three tang receiving slots, wherein each of said tangs is hingedly disposed in a respective one of said tang receiving slots.

10. An endoscopic bioptome, comprising:

a) a tubular member having a proximal end and a distal end;

b) a control member having a proximal end and a distal end, said control member extending through said tubular member;

c) proximal actuation means coupled to said proximal end of said tubular member and said proximal end of said control member for moving said control member axially within said tubular member;

d) a discrete cylindrical member having a distal edge and being coupled to one of said distal end of said tubular member and said distal end of said control member; and e) a jaw assembly including at least three jaws, each terminating with a distal jaw cup, wherein said jaw assembly is coupled to the other of said distal end of said tubular member and said distal end of said control member, such that movement of said control member within said tubular member moves one of said cylindrical member and said jaw assembly relative to the other such that said distal edge of said cylindrical member contacts said jaws and causes said jaws to move from a first open position to a second closed position.

11. An endoscopic bioptome according to claim 10, wherein said jaw assembly further includes:

a base member coupled to said other of said distal end of said tubular member and said distal end of said control member, and a washer, said washer securing said at least three jaws to said base member.

12. An endoscopic bioptome according to claim 10, wherein:

said jaws are made from a resilient material.

13. An endoscopic bioptome according to claim 10, wherein:

said jaws are substantially identical.

14. An endoscopic bioptome according to claim 10, wherein:

said jaws substantially form a hemisphere when in the closed position.

15. An endoscopic bioptome to claim 10, wherein:

said jaw cups each have a plurality of teeth.

16. An endoscopic bioptome to claim 10, wherein:

said jaw cups are not identical to each other.

17. An endoscopic bioptome according to claim 10, wherein:

said control member is a control wire.

18. An endoscopic bioptome according to claim 10, wherein:

said jaw assembly includes exactly three jaws.

19. An endoscopic bioptome according to claim 18, wherein:

each of said three jaws is includes a jaw cup provided with a tooth having an apex angle of approximately 120°.

20. An endoscopic bioptome, comprising:

a) a tubular member having a proximal end and a distal end;

b) a control member having a proximal end and a distal end, said control member extending through said tubular member;

c) proximal actuation means coupled to said proximal end of said tubular member and said proximal end of said control member for moving the control member axially within the tubular member;

d) a clevis having three radial slots, said clevis being coupled to said distal end of said tubular member;

e) three substantially rigid jaws, each jaw having a distal jaw cup and a proximal tang, said proximal tang being hingedly coupled to said clevis in a respective one of said three radial slots and said proximal tang being coupled to said control member, such that movement of said control member relative to said tubular member causes the jaws to move from a first open position to a second closed position.

21. An endoscopic bioptome according to claim 20, further comprising:

f) three links, each link being hingedly coupled to said control member and to a respective one of said tangs.

22. An endoscopic bioptome according to claim 20, wherein:

said three jaws are substantially identical.

* * * * *